United States Patent
Liu et al.

(10) Patent No.: US 9,556,106 B2
(45) Date of Patent: Jan. 31, 2017

(54) PURIFICATION OF CADAVERINE USING HIGH BOILING POINT SOLVENT

(71) Applicants: CATHAY R&D CENTER CO., LTD., New District, Shanghai (CN); CATHAY INDUSTRIAL BIOTECH LTD., Grand Cayman (KY)

(72) Inventors: Xiucai Liu, Shanghai (CN); Charlie Liu, Shanghai (CN); Duanfang Dai, Shanghai (CN); Bingbing Qin, Shanghai (CN); Naiqiang Li, Shanghai (CN)

(73) Assignees: CATHAY R&D CENTER CO., LTD., Shanghai (CN); CATHAY INDUSTRIAL BIOTECH LTD., Shanghai (CN)

( * ) Notice: Subject to any disclaimer, the term of this patent is extended or adjusted under 35 U.S.C. 154(b) by 0 days.

(21) Appl. No.: 14/764,109

(22) PCT Filed: Jan. 28, 2013

(86) PCT No.: PCT/CN2013/071045
§ 371 (c)(1),
(2) Date: Jul. 28, 2015

(87) PCT Pub. No.: WO2014/114000
PCT Pub. Date: Jul. 31, 2014

(65) Prior Publication Data
US 2015/0368185 A1 Dec. 24, 2015

(51) Int. Cl.
*C07C 209/84* (2006.01)
*C12P 13/00* (2006.01)

(52) U.S. Cl.
CPC .......... *C07C 209/84* (2013.01); *C12P 13/001* (2013.01)

(58) Field of Classification Search
CPC .................... C07C 209/84; C12P 13/001
See application file for complete search history.

(56) References Cited

U.S. PATENT DOCUMENTS

2010/0292429 A1   11/2010   Völkert et al.

FOREIGN PATENT DOCUMENTS

EP   2 543 736 A1   1/2013
JP   2009-028045 A   2/2009

OTHER PUBLICATIONS

International Search Report, PCT/CN2013/071045, Mailed Oct. 31, 2013, 3 pages.

*Primary Examiner* — Shailendra Kumar
(74) *Attorney, Agent, or Firm* — Rothwell, Figg, Ernst & Manbeck, P.C.

(57) ABSTRACT

One aspect of the invention relates to a method for the purification of cadaverine from an aqueous cadaverine composition comprising one or more involatile impurities, the method comprising obtaining cadaverine from evaporation or distillation of the aqueous cadaverine composition wherein one or more solvents are added to the evaporation/distillation system before the evaporation/distillation starts, during the evaporation/distillation and/or after the evaporation/distillation substantially stops when no more evaporation/distillation is observed; wherein the one or more solvents comprise at least one or more high boiling point (HBP) solvents. In certain embodiments, cadaverine may be evaporated/distilled at an unexpectedly lower heating temperature for an unexpectedly shorter heating time to provide a desired yield. Because cadaverine may decompose at high temperature, the unexpectedly lower heating temperature and unexpectedly shorter heating time decrease the undesired cadaverine decomposition. The methods disclosed herein provides unexpected high recovery rate (~100%) in the evaporation/distillation of cadaverine at a larger scale at a lower heating temperature compared to conventional distillation methods. Thus, the method disclosed herein will be highly appreciated in the industrial production of cadaverine.

22 Claims, 3 Drawing Sheets

PURIFICATION OF CADAVERINE USING HIGH BOILING POINT SOLVENT

CROSS-REFERENCE OF THE RELATED APPLICATION

The present application is a 35 U.S.C. §371 National Phase Entry Application of PCT/CN2013/071045, filed 28 Jan. 2013, designating the United States. The application is incorporated herein by reference in its entirety.

TECHNICAL FIELD OF THE INVENTION

The invention relates to methods for purification of cadaverine from cadaverine salt compositions. More specifically, the invention relates to methods for purification of bio-based cadaverine from bio-based productions thereof.

BACKGROUND

Bio-based cadaverine is a valuable platform chemical involved in the production of partially or fully bio-based products, such as partially or fully bio-based Nylon 56 and Nylon 510. Bio-based cadaverine can be synthesized via lysine decarboxylation of lysine in microorganisms. One way to separate and purify cadaverine from the bio-based production includes evaporation/distillation of cadaverine from an aqueous cadaverine composition. However, the cadaverine fermentation broth or enzymatic conversion solution may comprise involatile impurities that interfere with the cadaverine evaporation/distillation. Thus, the cadaverine evaporation/distillation may require high heating temperature and long evaporation/distillation time, while the cadaverine recovery yield is still relatively low and may contain undesired contaminations.

Thus, there is a need to provide a purification method of cadaverine (e.g. bio-based cadaverine) in the presence of involatile impurities with improved recovery yield and cadaverine quality.

SUMMARY OF THE INVENTION

One aspect of the invention relates to a method for the purification of cadaverine from an aqueous cadaverine composition comprising one or more involatile impurities, the method comprising:

a) obtaining cadaverine from evaporation or distillation of the aqueous cadaverine composition wherein one or more solvents are added to the evaporation/distillation system before the evaporation/distillation starts, during the evaporation/distillation and/or after the evaporation/distillation substantially stops when no more evaporation/distillation is observed; wherein the one or more solvents comprise at least one or more high boiling point (HBP) solvents.

BRIEF DESCRIPTION OF THE FIGURES AND DRAWINGS

Figure 1:
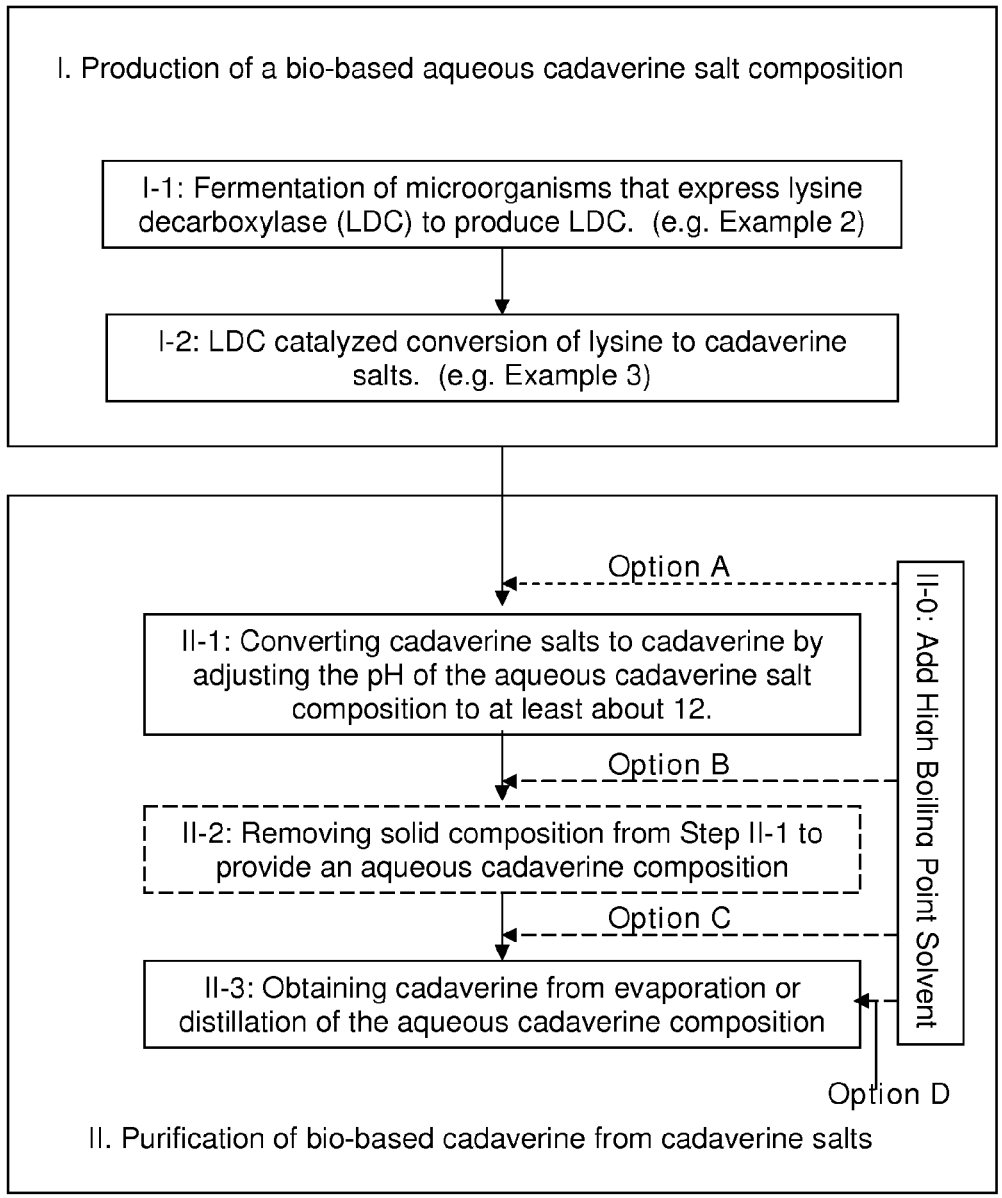

FIG. 1: A flow chart showing an embodiment according to a method disclosed herein.

Figure 2:
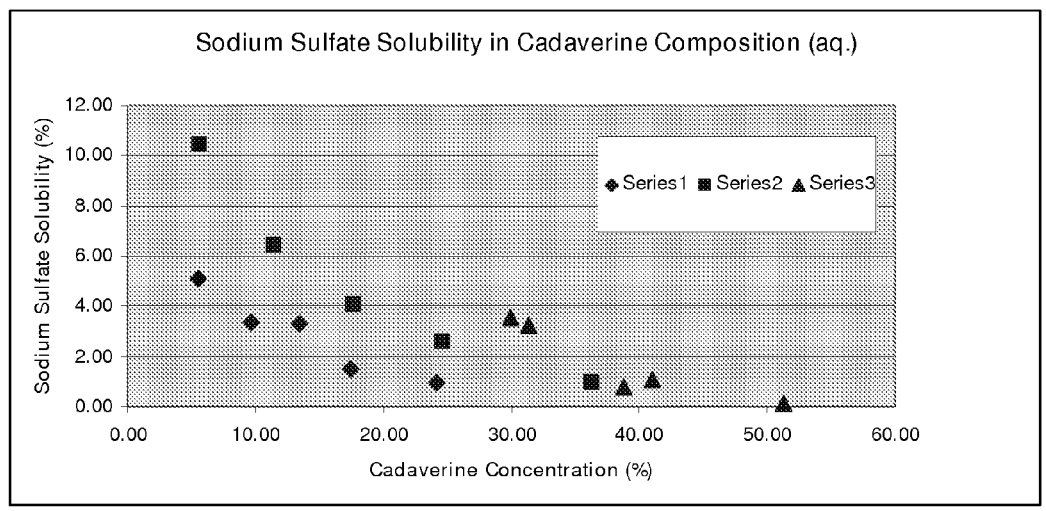

FIG. 2: Sodium sulfate solubility curves in cadaverine composition (aq.) at 5° C. (Series 1); 18° C. (Series 2); and 65° C. (Series 3).

Figure 3:
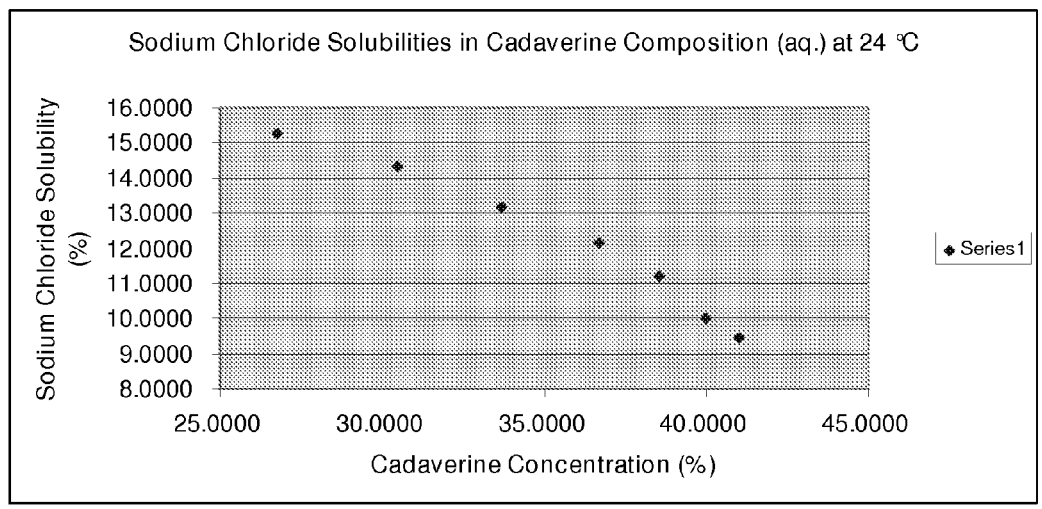

FIG. 3: Sodium chloride solubility curve in cadaverine composition (aq.) at 24° C. (Series 1).

DETAILED DESCRIPTION OF THE INVENTION

Bio-based cadaverine production can be produced via fermentation process or enzymatic conversion of lysine (e.g. as shown in Block I, FIG. 1). As used herein, a "bio-based" compound means the compound is considered bio-based under Standard ASTM D6866. In the fermentation process, microorganisms that produce lysine and express lysine decarboxylase (LDC) are fermented to produce cadaverine. In the enzymatic conversion of lysine, lysine/lysine salt can be converted to cadaverine catalyzed by LDC (e.g. Block I-2, FIG. 1; and Example 3). In one embodiment, the LDC is produced by fermenting microorganisms that express lysine decarboxylase (LDC) (e.g. Block I-1, FIG. 1; and also Example 2). The product obtained from the LDC catalyzed conversion of lysine is usually one or more cadaverine salts, which may be converted to cadaverine by adjusting the pH to about 12 or higher (Block II-1, FIG. 1).

Cadaverine has a relatively low boiling point and is relatively easy to evaporate/distil. However, the raw production mixture may contain involatile inorganic and/or organic impurities that are soluble/dispersible in water. Such impurities may significantly interfere the cadaverine evaporation/distillation, particularly as water is removed from the aqueous cadaverine composition. The inorganic impurities may comprise one or more inorganic salts. The organic impurities may include carbohydrates, protein and/or other organic residues that are involved in the fermentation processes. As used herein, an evaporation/distillation system is a heated composition during the evaporation/distillation. The fluidity of an evaporation/distillation system will decrease when more and more water/cadaverine is evaporated/distilled from the evaporation/distillation system. It will require a long heating time at high heating temperature to provide a desired cadaverine recovery yield from the evaporation/distillation system with lower fluidity. One or more organic solvents may be added into the evaporation/distillation system to improve fluidity, and the evaporation/distillation at a lower heating temperature and/or for a shorter heating time can provide a better cadaverine recovery yield and/or a better cadaverine quality (e.g. Block II-0, FIG. 1, wherein the solvent can be added at one or more of the options A, B, C, and D). In certain embodiments, part of the impurities may be optionally precipitated and/or removed from the evaporation/distillation system (e.g. Block II-2, FIG. 1). In certain embodiments, the methods disclosed herein have improved industrial applicability with the lowered heating temperature and shortened heating time. In certain embodiments, the organic solvent further comprises a low boiling point organic solvent.

A) Evaporation/Distillation Facilitated with Solvent Addition

One aspect of the invention relates to a method for the purification of cadaverine from an aqueous cadaverine composition comprising one or more involatile impurities, the method comprising:

a) obtaining cadaverine from evaporation or distillation of the aqueous cadaverine composition wherein one or more solvents are added to the evaporation/distillation system before the evaporation/distillation starts (e.g. Option C, FIG. 1), during the evaporation/distillation and/or after the evaporation/distillation substantially stops (i.e., when no more evaporation/distillation is observed) (e.g. Option D, FIG. 1);

wherein the one or more solvents comprise at least one or more high boiling point (HBP) solvents.

In certain embodiments, the one or more solvents are added to the evaporation/distillation system to improve and/or maintain the fluidity of the evaporation/distillation system during the evaporation/distillation. In general, a desired fluidity is a fluidity that the whole or substantially whole evaporation/distillation system can flow. The amount of the one or more solvents used may depend on the type of the one or more solvents and the amount and/or components of the evaporation/distillation system. A person of ordinary skill in the art would know how to determine the amount needed. In one example, the amount of the one or more solvents is at least about 0.1 times, at least about 1 time, at least about 2 times, at least about 5 times, at least about 7 times, or at least about 10 times of the starting amount of cadaverine in the evaporation/distillation system (by weight).

An evaporation/distillation system evaporated/distilled according to the novel methods disclosed herein, compared to an evaporation/distillation system evaporated/distilled without the addition of the one or more solvents, can provide a substantially similar (±10%) or higher cadaverine recovery yield while evaporated/distilled at a lower heating temperature for a shorter heating time. The differences in the heating temperatures, the heating times, and/or the recovery yield depend on the amount and/or the components of the evaporation/distillation system, and the one or more solvents used. In one embodiment, the heating temperature difference may be at least about 10° C., at least about 20° C., at least about 40° C., at least about 30° C., at least about 50° C., at least about 60° C., at least about 80° C., at least about 100° C., or about 20° C. to about 100° C. The shorter heating time may be no more than about 50% of the longer heating time, no more than about 30% of the longer heating time, or no more than 10% of the longer heating time.

A person of ordinary skill in the art will appreciate such improvements especially when the methods disclosed herein are used in an industrial evaporation/distillation. In certain embodiments, the method is used wherein the evaporation/distillation system is at least about 50 kg, at least about 100 kg, at least about 200 kg, at least about 500 kg, or at least about 1000 kg. An evaporation/distillation system evaporated/distilled according to the novel methods disclosed herein, compared to an evaporation/distillation system evaporated/distilled without the addition of the one or more solvents, when evaporated/distilled for similar or shorter time (no more than about 50% of the longer heating time, no more than about 30% of the longer heating time, or no more than 10% of the longer heating time) and at similar or lower heating temperature (lower by at least about 10° C., at least about 20° C., at least about 40° C., at least about 30° C., at least about 50° C., at least about 60° C., at least about 80° C., at least about 100° C., or about 20° C. to about 100° C.), the yield of the method disclosed herein is at least about 110%, at least about 120%, at least about 130%, at least about 140%, at least about 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, or at least about 400% of the yield of the method without the addition of the one or more solvents.

Cadaverine can be evaporated/distilled from the aqueous cadaverine composition via any suitable evaporation/distillation method/equipments. Examples include, without limitation, multi-effect evaporator, and fractional distillation/rectification equipments.

Each evaporation/distillation may be carried out at a reduced pressure or ambient pressure, although the reduced pressure is preferred. The first distillate obtained from the first evaporation/distillation comprises cadaverine and water. Then the first distillate (cadaverine/water mixture) is further distilled to provide cadaverine with higher purity. Each evaporation/distillation process can be accomplished using any suitable method/equipment (e.g. evaporation, multi-effect evaporation, and rectification).

In one embodiment, the heating temperature is about 50° C. to about 250° C., about 50° C. to about 80° C., about 70° C. to about 185° C., about 70° C. to about 120° C., about 75° C. to about 120° C., about 75° C. to about 130° C., about 75° C. to about 135° C., about 80° C. to about 120° C., or about 80° C. to about 180° C. The distillation pressure is about 5 kg or less (gauge pressure), a pressure lower than the ambient pressure (gauge pressure), about 0.02 MPa or lower (absolute pressure), about 0.015 MPa or lower (absolute pressure), about 0.005 MPa or lower (absolute pressure), or about 0.004 MPa or lower (absolute pressure).

The heating temperature depends on the distillation pressure. In general, the lower the distillation pressure, the lower the heating temperature. In one embodiment, the purified cadaverine is obtained from heating the aqueous cadaverine composition with an oil bath (120° C.) under vacuum (−0.096 MPa), with an oil bath (135° C.) under vacuum (−0.095 MPa), or with an oil bath (180° C.) under vacuum (−0.085 MPa).

In certain embodiments, the same or different one or more solvents may be added to the evaporation/distillation system multiple times before the evaporation/distillation starts, during the evaporation/distillation and/or after the evaporation/distillation substantially stops.

The high boiling point solvent may comprise any polar solvents, nonpolar solvents, or any combinations thereof, and has a boiling point higher than that of cadaverine. The high boiling point solvent is substantially unreactive under the evaporation/distillation condition and does not affect the quality of the purified cadaverine obtained from step a) above. As used herein, a substantially unreactive solvent means less than about 2% of the solvent reacts with cadaverine during the evaporation/distillation. In certain embodiments, the solvent added further comprises solvents having low boiling point (e.g. about 180° C. at 1 atm or lower).

In one embodiment, the boiling point of the high boiling point solvent is at least about 185° C. (1 atm), at least about 190° C. (1 atm), or about 190 to 260° C. (1 atm). The boiling point of cadaverine is about 179° C. (1 atm). In one embodiment, a high boiling point solvent having a boiling point of at least about 5° C. higher than that of cadaverine is used. In another embodiment, a high boiling point solvent having a boiling point of at least about 10° C. higher than that of cadaverine is used.

In another embodiment, the high boiling point solvent has a melting point that is no more than about room temperature (about 25° C.). In another embodiment, the high boiling point solvent has a melting point that is no more than about 80° C.

Examples of the high boiling point solvent include, without limitation, alkanes, chloroalkanes, benzene derivatives, alcohols, ethers, amines, esters, nitriles, and any combinations thereof.

Examples of suitable alkanes include, without limitation, $C_a$ alkanes, a=11, 12, 13, 14, 15, 16, 17, 18, 19, 20 (e.g. dodecane, tetradecane, . . . and mixtures thereof). Examples of suitable chloroalkanes include, without limitation, $C_a$ alkanes substituted with one or more chloro groups, a=12, 13, 14, 15, 16, 17, 18, 19, or 20 (e.g. 1-chloro-dodecane, 1-chloro tetradecane, and mixtures thereof). Examples of suitable benzene derivatives include, without limitation, benzene substituted with one or more $C_a$ alkyl groups, a=11, 12, 13, 14, 15, or 16, or chloro derivatives thereof (e.g. dodecyl benzene, tetradecyl benzene, dichlorotoluene, and combinations thereof), biphenyl, and combinations thereof. Examples of suitable alcohols include, without limitation, $C_b$ alcohols, b=8, 9, 10, 11, 12, 13, 14, 15, 16, 17, 18, 19, or 20 (e.g. 1-octanol, dodecanol, tetradecanol, glycerol, and combinations thereof). Examples of suitable ethers include, without limitation, diphenyl ether. Examples of suitable amines include, without limitation, $C_c$ amines having one or more amino groups, c=10, 11, 12, 13, 14, 15, 16, 17, 18, 19, or 20 (e.g. hexanediamine, decanediamine, and combinations thereof). Examples of suitable esters include, without limitation, diethyl succinate, diethyl adipate, and combinations thereof. Examples of suitable nitriles include, without limitation, butane dinitrile, hexane dinitrile, and combinations thereof. As used herein, unless otherwise specified, the hydrocarbon moieties of the suitable high boiling point solvents may be saturated or unsaturated with one or more double bonds and/or one or more triple bonds, and may be straight chain or branched chain. In certain embodiments, the high boiling point solvent does not comprise any alcohols.

The high boiling point solvent can be one organic solvent, or a mixture of multiple organic solvents of the same or different chemical types, as long as the solvents of a mixture are substantially unreactive among each other. For example, a mixture of octanol, butane dinitrile and dimethyl adipate can be used as the high boiling point solvent. In another example, a mixture of $C_{11}$ alkane and $C_{14}$ alkane (1:1 by weight) is used as the high boiling point solvent.

In one embodiment, the involatile impurities significantly hinder the evaporation of cadaverine from the cadaverine evaporation/distillation system.

Examples of the involatile impurities include, without limitation, inorganic impurities (e.g. salts such as sulfates, chlorides, phosphates and combinations thereof), and organic impurities (e.g. carbohydrates, proteins, cells and fragments thereof).

I) Aqueous Cadaverine Composition

In certain embodiments, the aqueous cadaverine composition is obtained from the following steps:
 a0-1) providing an aqueous cadaverine salt composition;
 a0-0) optionally adding one or more high boiling point solvents; and
 a1) adjusting the pH of the aqueous cadaverine salt composition to provide an aqueous cadaverine composition having a pH of at least about 12.

In certain embodiments, the aqueous cadaverine composition is obtained from the following steps:
 a0-2) providing an aqueous cadaverine salt composition comprising a cadaverine production composition, wherein the cadaverine production composition is obtained from a bio-based cadaverine production process;
 a0-0) optionally adding one or more high boiling point solvents; and
 a1) adjusting the pH of the aqueous cadaverine salt composition to provide an aqueous cadaverine composition having a pH of at least about 12.

In certain embodiments, the pH of the aqueous cadaverine composition in step a1) is about 14 or higher.

1) Aqueous Cadaverine Salt Compositions

An aqueous cadaverine salt composition comprises a cadaverine salt and/or a fully or partially protonated cadaverine. In one embodiment, the pH of the aqueous cadaverine salt composition is no more than about 12, no more than about 11, no more than about 10 or lower, no more than about 9, or about 7 to about 8. In another embodiment, the cadaverine salt is formed from cadaverine and one or more acids selected from the group consisting of organic acid, inorganic acids, and any combinations thereof. Examples of the inorganic acids include, without limitation, hydrochloride, sulfuric acid, carbonic acid, and phosphoric acid. Examples of the organic acids include, without limitation, hexdicarboxylic acid, and acetic acid. In another embodiment, the aqueous cadaverine salt composition comprises acid anions. Examples of the acid anions include, without limitation, $Cl^-$, $SO_4^{2-}$, $^-OOC(CH_2)_3COO^-$, $CH_3COO^-$, $CO_3^{2-}$, $PO_4^{3-}$, and any combinations thereof. As used herein, cadaverine chloride is cadaverine chloride, cadaverine dihydrochloride, or a mixture thereof.

In another embodiment, the aqueous cadaverine salt composition comprises a cadaverine production composition obtained from a bio-based cadaverine production process.

Examples of the bio-based cadaverine production process include, without limitation, fermentative production and in vitro enzymatic production. In certain embodiments, the cadaverine production compositions obtained from the bio-based cadaverine production have a pH of no more than about 12, no more than about 11, no more than about 10 or lower, no more than about 9, or about 7 to about 8, wherein most of the cadaverine in the cadaverine production composition is presented in a salt form.

a) Enzymatic Production of Bio-Based Cadaverine

In one embodiment, the aqueous cadaverine salt composition comprises a cadaverine production composition obtained from an enzymatic bio-based cadaverine production process. The enzymatic bio-based cadaverine production process comprises converting lysine and/or a lysine salt (lysine/lysine salt) to cadaverine in the presence of lysine decarboxylase (LDC). In one example, the production is carried out in an aqueous media.

i) Lysine/Lysine Salt

The lysine salts are salts formed from lysine and one or more acids selected from the group consisting of inorganic acids, organic acids, and any combinations thereof. In certain embodiments, the lysine salts are one or more lysine/inorganic acid salts. Examples of lysine/inorganic acid salts include, without limitation, lysine hydrochloride, lysine sulfate and any combinations thereof.

Lysine/lysine salt can be prepared from any suitable fermentative production, and the lysine fermentation broth obtained therefrom can be used in the enzymatic production of bio-based cadaverine. In one embodiment, the lysine fermentation broth comprises an aqueous lysine sulfate solution. In another embodiment, the lysine fermentation broth is further processed before use in the enzymatic bio-based cadaverine production. For example, the lysine fermentation broth can be further processed (e.g. via filtration, centrifuge or membrane-filtration) to remove impurities (e.g. microbes) and provide the aqueous lysine salt solution. In one example, an aqueous lysine sulfate solution is obtained from the lysine fermentation process. The aqueous lysine sulfate solution is further processed using ion-exchange resin, wherein the eluate is neutralized with hydrochloride acid to provide aqueous lysine hydrochloride solution. In another example the lysine fermentation broth is decolored with activated carbon and filtered to provide aqueous lysine sulfate solution.

Commercially available lysine/lysine salt products (e.g. lysine hydrochloride) may also be used in the enzymatic bio-based cadaverine production. In one embodiment, a lysine fermentation broth obtained from the fermentation process is used in the enzymatic bio-based cadaverine production.

Any microbes suitable for lysine fermentation can be used herein. Examples of the microbes include, without limitation, wild-type strains, induced mutant strains, and/or recombinant strains. Examples of the strains include, without limitation, *Corynebacterium* strains (e.g. *C. glutamicum, C. pekinense*, and *C. crenatum*), and *Brebvibacterium* strains (e.g. *B. lactofermentum* and *B. flavum*).

The lysine fermentation process is carried out in a medium. Such a medium can be any medium suitable for the fermentation. For example, the medium may contain carbon sources and non-carbon nutrient sources. Examples of the carbon sources include, without limitation, sugar (e.g. carbohydrates such as glucose and fructose), oil and/or fat, a fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of the derivatives of a fatty acid include, without limitation, esters and salts thereof. Examples of the non-carbon sources include, without limitation, nitrogen sources (e.g. beef extract, yeast extract and corn steep liquor), inorganic salts, and other organic nutrient sources.

Examples of the nitrogen source may comprise ammonia, ammonium salts (e.g. ammonium chloride, ammonium sulfate and ammonium phosphate), tryptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like. The composition of the medium may be adjusted and optimized according to the type of strains and the product of the fermentation.

The fermentation may be carried out at any temperature at which the cells can grow, and preferably at about 20° C. to about 40° C., or about 35° C. The culture period may be about 1 day, about 2 days, about 3 days, about 4 days, about 5 days, about 6 days, about 7 days, about 8 days, about 9 days, or about 10 days.

ii) LDC

LDC is an enzyme that can convert lysine to 1,5-cadaverine. LDC may be prepared from any suitable fermentative production, and the LDC fermentation broth obtained therefrom can be used directly in the enzymatic production of bio-based cadaverine. In certain embodiments, the LDC fermentation broth may be further processed before use in the cadaverine enzymatic production. For example, the LDC fermentation broth may be centrifuged, filtered, or otherwise processed or further purified to provide processed or purified LDC compositions. Examples of the processed/purified LDC compositions include, without limitation, LDC fermentation cells and/or fragments thereof; LDC supernatant obtained from centrifuging or filtering the LDC fermentation broth; LDC supernatant obtained from removal of cells by centrifuge or filtration of the LDC fermentation broth; purified LDC and compositions thereof; and any combinations of more than one type of LDCs.

Any microbes suitable for LDC fermentation can be used herein. Examples of the microbes include, without limitation, wild-type strains, induced mutant strains, and/or recombinant strains. Examples of the strains include, without limitation, induced mutant *Escherichia coli*, induced mutant *Hafnia alvei*, and recombinant *Escherichia coli*, and recombinant *Hafnia alvei* (e.g. the recombinant *Hafnia alvei* disclosed in Chinese application 201210177392.X).

The LDC fermentation process is carried out in a medium. Such a medium can be any medium suitable for the fermentation. For example, the medium can be the same as or similar to the medium used in the lysine fermentation process, which contains carbon sources and non-carbon nutrient sources as described supra, and is optimized for the LDC fermentation.

The fermentation may be carried out at any temperature at which the cells can grow, and preferably at about 20° C. to about 40° C., or about 35° C. The culture period may be about 1 day, about 2 days, about 3 days, about 4 days, about 5 days, about 6 days, about 7 days, about 8 days, about 9 days, or about 10 days.

iii) Lysine Decarboxylation (LDCN) Reaction

Any suitable enzymatic production of bio-based cadaverine from lysine/lysine salt can be used herein. In an LDCN reaction, the substrate is lysine/lysine salt as described supra, and the enzyme is LDC as described supra. The reaction temperature may be from about 20° C. to about 60° C. The desired reaction pH is a pH that is suitable for the enzymatic conversion, and depends on the LDC used in the LDCN reaction. In certain embodiments, the suitable reaction pH may range from about 5 to about 8.

In one embodiment, an acid is added in the LDCN reaction to maintain the reaction pH within the suitable range. In one example, the acid is added in the lysine/lysine salt solution before adding LDC to adjust the pH to a suitable pH, then LDC is added to facilitate the conversion of lysine to cadaverine. In another example, the acid is added into the reaction after LDC is mixed with the lysine/lysine salt solution. Examples of suitable acids include, without limitation, inorganic acid (e.g. HCl, sulfuric acid, and any combinations thereof), and acidic gas (e.g. $CO_2$).

In another embodiment, a buffer is used in the LDCN reaction to maintain the pH within the suitable range to optimize the conversion yield. Examples of the buffers include, without limitation, common buffers used in the working range of LDC, e.g. 7 part 0.2 mol/L acetic acid plus 3 part 0.2 mol/L sodium acetate solution.

In another embodiment, the starting pH and the ending pH of the LDCN reaction are within the suitable pH range for the enzymatic conversion, and additional acid or other substance may or may not be added into the reaction for pH control.

In certain embodiments, the substrate and enzyme may be added in the reaction at more than one time, respectively. The manner of addition of enzyme and/or substrate can be adjusted to optimize the conversion of the enzymatic conversion.

In certain embodiments, cell immobilization technology is applied on LDC to improve the reaction yield. Any suitable cell immobilization method can be used, e.g. embedding method (e.g. calcium alginate embedding method).

In certain embodiments, other additives facilitating the enzymatic conversion may be present in the LDCN reaction mixture. Examples of such additives include, without limitation, inorganic salts and vitamins.

2) Adjusting the pH of an Aqueous Cadaverine Salt Composition to Provide an Aqueous Cadaverine Solution Having a pH of at Least about 12.

The aqueous cadaverine salt composition is as described supra. In one embodiment, the pH of the aqueous cadaverine salt composition is no more than about 12, no more than about 11, no more than about 10 or lower, no more than about 9, or about 7 to about 8.

In another embodiment, the aqueous cadaverine salt composition comprises a cadaverine production composition obtained from a LDCN reaction as described supra.

The pH of an aqueous cadaverine composition depends on the cadaverine concentration and the temperature (e.g. Table 1 of Example 5).

The pH of the aqueous cadaverine salt composition can be adjusted by adding one or more inorganic bases therein. A cadaverine salt reacts with the one or more inorganic bases to provide cadaverine and the corresponding one or more inorganic salts.

Examples of the one or more inorganic bases include, without limitation, hydroxides, such as alkaline metal hydroxides (e.g. NaOH, KOH, and a mixture thereof), alkaline earth metal hydroxides (e.g. $Mg(OH)_2$, $Ca(OH)_2$, and a mixture thereof), and basic salts thereof (e.g. sodium phosphate, potassium phosphate, sodium carbonate, potassium carbonate, and a mixture thereof). The one or more bases may be added into the aqueous cadaverine salt composition at substantially the same time or at different time. When more than one base is added, the different bases may be added as one or more mixtures or separately. In certain embodiments, the base mixtures may be a mixture of one or more strong bases and one or more weak bases. Examples of the base mixtures include, without limitation, a mixture of sodium phosphate and sodium hydroxide, and a mixture of sodium carbonate, sodium hydroxide and potassium hydroxide. In certain embodiments, the base mixtures may be a mixture of one or more strong bases. Examples of the base mixtures include, without limitation, a mixture of sodium hydroxide and potassium hydroxide.

Scheme 1 illustrates an example of the reaction wherein the cadaverine salt is a hydrochloride salt and the base is NaOH:

Scheme 1

$[NH_3(CH_2)_5NH_3]Cl_2 + 2NaOH \longrightarrow NH_2(CH_2)_5NH_2 + 2NaCl + 2H_2O$ A person of ordinary skill in the art would readily understand and appreciate other reactions wherein cadaverine and one or more inorganic salts are produced from reactions between one or more specific cadaverine salts and one or more specific bases. Examples of the one or more inorganic salts include, without limitation, sodium sulfate, sodium carbonate, NaCl, potassium sulfate, and KCl.

The one or more bases may be added as solid and/or as solution (e.g. aqueous solution).

The amounts of the one or more bases added depend on the amount of cadaverine in the aqueous cadaverine salt composition. The amounts of the one or more bases are suitable when a substantial amount of the cadaverine salt is converted to cadaverine. In certain embodiments, the pH of the resulting aqueous solution is no less than about 12, no less than about 13, no less than about 13.3, or no less than about 13.5.

The one or more bases may be added to and/or reacted with the aqueous cadaverine salt composition at any temperature that allows the production of cadaverine from the cadaverine salt. In general, the higher the reaction temperature, the faster the reaction runs.

In one embodiment, the base is an aqueous sodium hydroxide solution, the aqueous cadaverine salt composition is an aqueous cadaverine sulfate solution, the base is added at about 60° C. and the reaction almost completes immediately after the addition of the base, sodium hydroxide.

In another embodiment, the methods disclosed herein further comprise adding the one or more bases at a first temperature, and optionally reacting the reaction at a second temperature for about a first time. The first and the second temperatures can be the same or different. The first and/or the second temperature can be about 10° C. to about 80° C., about 40° C. to about 80° C., about 10° C., about 40° C., about 60° C., about 70° C., or about 80° C. The first reaction time is the time required to substantially convert amount of the cadaverine salt to cadaverine (i.e. remaining cadaverine salt concentration is no more than about 5%). A person of ordinary skill in the art would understand and appreciate how to determine the first reaction time. In certain embodiment, the first reaction time is about 0.01 to about 2 hours.

a) Removing a Solid Composition from the Aqueous Cadaverine Composition of Step a1).

In certain embodiments, the one or more inorganic salts cannot completely dissolve in the aqueous solution, and are precipitated from the aqueous solution as a solid composition. Thus, the aqueous cadaverine composition of step a1) comprises a solid composition and an aqueous solution, wherein the solid composition comprises the one or more inorganic salts, and the aqueous solution comprises cadaverine and the one or more inorganic salts. Step a1) optionally further comprises:

a1-1) Removing a Solid Composition from the Aqueous Cadaverine Composition of Step a1).

As used herein, unless otherwise specified, all concentrations are concentrations by weight (w/w).

In general, the higher the cadaverine concentration in an aqueous solution, the lower the solubility of an inorganic salt therein is. (See, FIGS. 1 and 2, the solubility curves of NaCl and $Na_2SO_4$ in an aqueous cadaverine composition at different cadaverine concentrations, respectively.)

Although any concentration of the aqueous cadaverine salt composition may be suitable for this method, in certain embodiments, the solid composition is removed from the aqueous cadaverine composition wherein the cadaverine concentration of the aqueous cadaverine composition is about 5% or higher, about 10% or higher, about 15% or higher, about 20% or higher, or about 30% or higher. In certain embodiments, optionally, step a1-1) further comprises the following steps before step a1-1) described supra is performed:

a1-11) concentrating the aqueous cadaverine salt composition before the addition of the one or more bases; and/or optionally a1-12) concentrating the aqueous cadaverine salt composition/base reaction after the addition of the one or more bases; and/or optionally a1-13) concentrating the aqueous cadaverine salt composition/base reaction during the addition of the one or more bases;

such that the cadaverine concentration of the aqueous cadaverine composition of step a) is about 5% or higher, about 10% or higher, about 15% or higher, about 20% or higher, or about 30% or higher.

In one embodiment, the aqueous cadaverine salt composition is a cadaverine sulfate solution obtained from a LDCN reaction; the base is NaOH. A cadaverine/$Na_2SO_4$ mixture is provided from the reaction of cadaverine sulfate and NaOH. When the cadaverine concentration of the aqueous solution of the cadaverine/$Na_2SO_4$ mixture is about 17% or higher, about 80% or more of the $Na_2SO_4$ is precipitated from the aqueous solution.

The solid composition may be separated from the aqueous cadaverine composition of step a1) by any method suitable to separate solid from liquid, e.g. centrifuge, and filtration.

In certain embodiments, the acid anion content of the aqueous cadaverine composition obtained from step a1-1) is no more than about 70%, no more than about 50%, or no more than about 30% of that of the cadaverine salt composition.

In general, the lower the solution temperature, the lower the solubility of an inorganic salt therein is. As shown in FIG. 2, at about the same cadaverine concentration (e.g. about 20%), sodium sulfate solubility at a higher temperature (18° C.) is more than that at a lower temperature (5° C.). FIG. 2 also showed that when the cadaverine concentration is relatively high (e.g. about 30% or higher, or about 40% or higher), sodium sulfate solubility is low even at a relatively high temperature (e.g. 65° C.).

In certain embodiments, the methods disclosed herein optionally further comprise:

a1-21) maintaining the first composition at a third temperature for a second time before the performance of step a1-1).

The third temperature can be from about 2° C. to about 80° C., about 2° C., about 4° C., about 5° C., about 10° C., about 15° C., about 35° C., about 38° C., about 40° C., about 50° C., or about 65° C. In certain embodiments, the third temperature is not higher than the first and/or the second temperature described supra. In certain embodiments, the third temperature is lower than the second temperature to facilitate the precipitation of the one or more inorganic salts from the aqueous solution of step a1).

In certain embodiments, step a1-1) disclosed herein comprises:

a1-31) filtering/centrifuging the first composition to provide a solid and a filtrate/supernatant;

a1-32) rinsing the solid with an aqueous salt solution and filtering/centrifuging the obtained mixture to provide another solid and another filtrate/supernatant;

a1-33) optionally repeating step a1-32) until the solid obtained is substantially free of cadaverine; and a1-34) combining the filtrates/supernatants obtained from steps a1-31), a1-32) and a1-33) to provide the aqueous cadaverine composition to be further processed in step a).

In certain embodiments, the aqueous salt solution used in the rinse of each step a1-32) can be the same or different. Examples of such aqueous salt solution include, without limitation, saturated aqueous salt solutions (e.g. NaCl saturated aqueous solution, and sodium sulfate saturated aqueous solution).

In certain embodiments, the temperature at which steps a1-31) and a1-32) are performed can be the same or different, and can be the third temperature described above.

In one embodiment, the aqueous cadaverine salt composition is cadaverine sulfate, the base is NaOH, and the first and the second temperatures are 60° C. When the third temperature is 35° C., in the obtained aqueous solution, the cadaverine concentration is about 20%, and the concentration of $SO_4^{2-}$ is about 3% or lower.

In another embodiment, the aqueous cadaverine salt composition is cadaverine sulfate, the base is NaOH, the first and the second temperatures are 10° C. In the obtained aqueous solution, the cadaverine concentration of the aqueous solution of resulting reaction is about 10%. When the third temperature is about 2° C., and the second time is about 1 hour, the concentration of $SO_4^{2-}$ is about 3.5% or lower.

In another embodiment, the aqueous cadaverine salt composition is cadaverine sulfate, the base is NaOH, the first and the second temperatures are 80° C. The third temperature is 40° C., and the second time is about 1 hour. In the obtained aqueous solution, the cadaverine concentration of the aqueous solution of resulting reaction is about 30%, and the concentration of $SO_4^{2-}$ is about 2% or lower.

B) Advantages

The methods disclosed herein improve the cadaverine evaporation/distillation from an aqueous cadaverine composition comprising involatile impurities by adding one or more solvents into the cadaverine evaporation/distillation system. The addition of the one or more solvents improves the fluidity of the cadaverine evaporation/distillation system, and thus facilitate the cadaverine evaporation/distillation thereof. The improved cadaverine fluidity results in an unexpectedly lower heating temperature and an unexpectedly shorter heating time to provide a desired evaporation/distillation yield. Because cadaverine may decompose at high temperature (e.g., Example 18), the unexpectedly lower heating temperature and unexpectedly shorter heating time decrease the undesired cadaverine decomposition.

In certain embodiments, the methods disclosed herein significantly reduce the heating temperature for the cadaverine evaporation/distillation despite of the impurities that interfere with evaporation/distillation. In one example (Example 12), a first aqueous cadaverine sulfate composition (21.36%, 252.07 g) was converted to a first aqueous cadaverine composition without further salt-reduction treatment of step a1-1). The distillation of the first aqueous cadaverine composition was performed with the addition of $C_{14}/C_{11}$ alkane mixture (1/1). The distillation was carried out with a heating temperature of from about 80° C. to about 130° C. (oil bath) at a pressure of no lower than −0.096 MPa, and the recovery yield was 86.68% (Example 12). In another example (Example 14), a second aqueous cadaverine sulfate composition (28.52%, 150 g) was converted to a second aqueous cadaverine composition without further salt-reduction treatment of step a1-1). The distillation of the first aqueous cadaverine composition was performed without the addition of another solvent. The distillation was carried out with a heating temperature of from about 80° C. to about 180° C. (oil bath) at a pressure of no lower than −0.095 MPa, and the recovery yield was 77.52% (Example 14). In another example (Example 14), a second aqueous cadaverine sulfate composition (28.52%, 150 g) was converted to a second aqueous cadaverine composition with further salt-reduction treatment of step a1-1). The distillation of the first aqueous cadaverine composition was performed without the addition of another solvent. The distillation was carried out with a heating temperature of from about 80° C. to about 180° C. (oil bath) at a pressure of no lower than −0.095 MPa, and the recovery yield was 93.26% (Example 14).

In certain embodiments, the methods disclosed herein significantly increase the cadaverine recovery yield when the aqueous cadaverine evaporation/distillation system comprises significant amount of inorganic salts. As discussed above, without the salt-reduction treatment of step a1-1), the cadaverine evaporation/distillation yield with addition of other solvent (86.68%, Example 12) is significantly higher than the cadaverine evaporation/distillation yield without addition of other solvent (77.52%, Example 14).

Furthermore, the unexpectedly lower heating temperature and unexpectedly shorter heating time are especially appreciated for an industrial cadaverine evaporation/distillation. Because of the difficulties of stirring and heat-transfer, the lack of fluidity in the evaporation/distillation system presents a more significant problem when the scale is relatively large (e.g. about 50 kg, at least about 100 kg, at least about 200 kg, at least about 500 kg, or at least about 1000 kg). In certain embodiments, the evaporation/distillation system (about 100 kg cadaverine composition) provides a 20% recovery rate after distilled in a 150 L distillator in an oil bath (200° C.) at a reduced pressure (−0.095 MPa) for 10 hours (Example 15). The evaporation/distillation system is substantially solid, and cannot be stirred. The evaporation/distillation residue after the evaporation/distillation substantially stops cannot be discharged from the distillator because it is substantially solid without fluidity. In certain embodiments, the evaporation/distillation system (about 200 kg cadaverine composition) provides a 33.87% recovery rate after distilled in an oil bath (increased from 80~180° C. in 130 min) at a reduced pressure (−0.095 MPa) (Example 15). However, methods disclosed herein provides an unexpected high recovery rate (~100%) in the evaporation/distillation of cadaverine at a similar scale from a similar cadaverine composition at an unexpectedly lower heating temperature (130° C.) (Example 16).

C) Examples

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

Lysine was detected according to the standard method for determination of food additive L-lysine hydrochloride (GB10794-2009). Sulfate ion was detected according to the standard method for determination of industrial anhydrous sodium sulfate (GB6009-92). Other ions were detected by ion chromatography. Cadaverine was detected according to the cadaverine characteristic absorption near 2.5 ppm in NMR spectrum. DMSO was used as the internal standard. Cadaverine salt compositions were also characterized by cadaverine concentration by adjusting the pH of the test sample to at least about 14 before NMR spectrums were taken.

Bio-based aqueous cadaverine salt compositions were prepared according to the methods disclosed in Examples 1, 2, and 3. Other approaches may also be used in transformation of lysine into cadaverine by microorganisms. (See, e.g., "Study on the transformation of 1-lysine into cadaverine by microorganism," Jing Zhu, Master Thesis, Tianjin University of Science and Technology, March, 2009). Example 4 describes a conventional extraction purification of cadaverine from a cadaverine salt composition. Example 5 shows the changes of pH of cadaverine aqueous solution when the cadaverine concentration changes. Examples 6 and 7 show the effective salt reduction from a few embodiments according to the novel methods disclosed herein. Example 8 is the measurement of the solubilities of NaCl and $Na_2SO_4$ in cadaverine aqueous solutions of different cadaverine concentrations. Examples 13 and 17 shows the effective cadaverine purification from an aqueous cadaverine sulfate composition prepared from purified cadaverine (purity 95.00%) using the novel methods disclosed herein with different solvents (e.g. alkane mixture in Example 13, and alcohol in Example 17). Examples 9-12 include cadaverine purifications from bio-based cadaverine salt compositions according to the novel methods disclosed herein, with different solvent addition manners (e.g. Example 9, using an alkane as the high boiling point solvent); and/or with different high boiling point solvents (e.g. alkanes in Examples 9 and 12, ether in Example 10, and alcohol in Example 11). Examples 14 and 15 describe cadaverine purifications from bio-based cadaverine salt compositions without solvent additions at different scales (e.g. a smaller scale in Example 14, and a larger scale in Example 15). Example 16 describes cadaverine purifications from bio-based cadaverine salt compositions according to the novel methods disclosed herein at a larger scale. Example 18 shows cadaverine may decompose after heated at 160° C., thus a shorter heating time will lower the possible decomposition of cadaverine and provide a higher recovery rate.

Example 1

Preparation of a Lysine Fermentation Broth (1) LB Medium Slants:
LB medium slants were prepared using LB medium containing tryptone 1%, yeast extract 0.5%, and NaCl 1%, pH 7.2.
(2) Primary Seed Culture Medium (Shake Flask Seed Culture Medium)
A *Corynebacterium* culture expressing lysine was grown on the LB medium slants, and transferred into a 500 mL seed flask containing the 200 mL liquid medium (liquid broth medium containing beef extract 1%, tryptone 1%, yeast extract 0.5%, and NaCl 0.5%, pH 7.0), then cultured at 33° C. on 200 rmp shaking bed for 10-15 hours.
(3) Lysine Fermentation
A fermentation medium (5 L) was added to a 10 L fermentor. Then the seed liquid prepared above was transferred into the fermentor for fermentation. The fermentation medium contained: glucose 1.5%, molasses 0.2%, corn steep liquor 0.06%, soybean meal hydrolysate 0.05%, ammonium sulfate 0.2%, dipotassium hydrogen phosphate 0.01%, and magnesium sulfate 0.005%. After sterilization at 121° C. for 20 minutes, the fermentor was rotated at 400-500 rpm at 31-33° C. for fermentation, the amount of air introduced to the fermentor was controlled at 0.5-1.2 vvm, DO>20%. In the process, a stream sugar was added to control the sugar concentration to about 0.5%; a stream of ammonium sulfate was added to control the ammonia concentration to about 0.1%; and a stream of ammonia was added to control the pH at about 6.5-6.8. Meanwhile, bubble enemy (glycerol polyoxypropylene polyoxyethylene ethers) was added to control bubbles in the fermentation process. The whole fermentation process lasted for about 41 hours. The tank liquid released had a lysine concentration of about 12%.

(4) Work-Up of the Lysine Fermentation Broth

The lysine fermentation broth was optionally further processed (e.g. filtered, centrifuged, and/or filtered through membrane) to remove the cells to obtain a clear liquid.

Example 2

Preparation of Lysine Decarboxylase (LDC)

(1) Seeds and Fermentation Medium:

Seed culture medium (g/L): Tryptone 10, beef extract 5, NaCl 5, corn steep liquor, 5, pH 7.2. A wild *Hafnia alvei* strain (*Hafnia alvei* 1.1009 from CGMCC, http://www.cgmcc.net/index.php/Contents/show/id/460) expressing LDC was grown on slant, transferred to a triangle flask containing 30 mL seed medium, and cultured at 35° C. with shaking at 170 R/min for 15 hour.

(2) Culture Conditions

Fermentation medium (g/L): glucose 18, yeast extract 20, corn steep liquor 36.6, $MgSO_4$ 0.3, $KH_2PO_4$ 0.1, NaCl 3, L-lysine 5, vitamin $B_6$ 1, and pH 6.5-7.0.

10% seed was transferred into a 250 mL flask containing 100 mL fermentation medium. In the cell growth phase, the temperature was controlled at 35° C. and the cells were cultured on a rotary shaker 200 r/min oscillation for 13 hours; then cultured statically for 5 hours. The obtained LDC fermentation broth was used directly in LDC catalyzed conversion of lysine or centrifuged to obtain wet cells.

Example 3

LDC Catalyzed Conversion of Lysine (1) Enzymatic Conversion of Lysine Hydrochloride 100 L LDC fermentation broth (Example 2) was added in a 250 L reactor, acetic acid and sodium acetate were added to the reaction to final molar concentrations of 0.2 mol/L, respectively. Commercially available lysine hydrochloride was added to the reaction to control the lysine concentration at 3 g/L, and Tween-80 (total 0.15 kg) was added to the reaction. The reaction was stirred at 35° C. The reaction was complete within about 5 hours, with a lysine molar conversion rate of about 98%. The enzymatic conversion s was concentrated to obtain a cadaverine salt solution (about 5%), which was ready for optional further processing.

(2) Enzymatic Conversion of Lysine Sulfate

100 L LDC fermentation broth (Example 2) was added in a 250 L reactor, acetic acid and sodium acetate were added to the reaction to final molar concentrations of 0.2 mol/L, respectively. Commercially available lysine sulfate (65%) was added to the reaction to control the lysine concentration at 3 g/L, and Tween-80 (total 0.15 kg) was added to the reaction. The reaction was stirred at 35° C. The reaction was complete within about 5 hours, with a lysine molar conversion rate of about 86%. The enzymatic conversion solution was concentrated to obtain a cadaverine salt solution (about 5%), which was ready for optional further processing.

(3) Enzymatic Conversion of Lysine Fermentation Broth

A 1670 gram of the above-prepared lysine fermentation broth (Example 1) was put into the above-prepared LDC fermentation broth (Example 2) to get 100 L of a mixture solution (lysine concentration at 2 g/L). Acetic acid and sodium acetate were added to the reaction to final molar concentrations of 0.2 mol/L, respectively, and Tween-80 (total 0.15 kg) was added to the reaction. The reaction was stirred at 35° C. The reaction was complete within about 8 hours, with a lysine molar conversion rate of about 83%. The enzymatic conversion solution was concentrated to obtain a cadaverine salt solution (about 5%), which was ready for optional further processing.

Example 4

Cadaverine Purification Using Organic Solvent Extraction

A cadaverine chloride enzymatic conversion solution (6% cadaverine) was concentrated by evaporation at a reduced pressure to provide an aqueous cadaverine chloride solution (1,075 L, 1,118 kg, and 9.83% cadaverine). Sodium hydroxide (aq., 30%, 332 L) was added to provide an aqueous cadaverine composition, pH 14. Saturated aqueous butanol solution was added to the above reaction for extraction (400 L). The extraction mixture was stirred/extracted at 50~60° C. for 40 minutes, and sit for 1 hours for the separation of aqueous and organic phases. The aqueous layer was further extracted twice with saturated butanol solution (aq. 400 L) as described above. The organic phases were combined and had a cadaverine concentration of 9%. The combined organic phase was concentrated at 50~60° C. at −0.085 MPa, and further distilled at 80~120° C. at −0.085 MPa for 6 hours to provide a cadaverine recovery yield of 62.35%.

Although the aqueous cadaverine composition was extracted before distillation, significant amount of impurities were still left in the system, which interfered the cadaverine distillation and provided a low cadaverine recovery yield.

Example 5 pH of Some Aqueous Cadaverine Compositions at Room Temperature

The pH of some aqueous cadaverine compositions at room temperature were detected using a pH meter (Table 1).

TABLE 1

The pH of some aqueous cadaverine compositions at room temperature

| Cadaverine Concentration (%) | pH |
|---|---|
| 1 | 12.29 |
| 4.91 | 12.59 |
| 9.9 | 12.74 |
| 19.8 | 12.89 |
| 30 | 13.4 |
| 50 | 14 |

Example 6

Salt-Reduction Processes (I)

A cadaverine sulfate enzymatic conversion solution (1000 g) was concentrated on a rotavap at 50 to 70° C. under −0.09 MPa to a first cadaverine sulfate composition (139.63 g). Another cadaverine sulfate enzymatic conversion solution (1000 g) was concentrated to a second cadaverine sulfate composition (161.00 g) under substantially the same condition. Sodium hydroxide (chemical grade, about 28.3 g) was added to the first cadaverine sulfate composition, and stirred until the pH was greater than 13.3. The mixture was filtered at about 65° C., and the filtered solid was flamed to provide a dry solid (44.38 g) containing 43.87 g sodium sulfate (98.85%). The same process was carried out on the second cadaverine sulfate composition, and the obtained dry solid (42.70 g) contained 42.16 g sodium sulfate (98.94%). Thus, this example showed that according to the methods disclosed herein, salt reduction in a more concentrated cadaverine salt composition was more efficient.

Example 7

Salt-Reduction Processes (II)

A first cadaverine sulfate enzymatic conversion solution (300.74 g, 4.6% cadaverine, 2.83% $SO_4^{2-}$) was concentrated on a rotavap at 50 to 70° C. under −0.09 MPa to a first cadaverine sulfate composition (120.13 g, 11.51% cadaverine, 7.08% $SO_4^2$). A second cadaverine sulfate enzymatic conversion solution (300.79 g, 4.6% cadaverine, 2.83% $SO_4^{2-}$) was concentrated to a second cadaverine sulfate composition (79.69 g, 17.36% cadaverine, 10.68% $SO_4^{2-}$) under substantially the same condition. Sodium hydroxide (aq., 18.05 g, 60%, about 1 equivalent) was added to the first cadaverine sulfate composition and filtered at about 65° C. to provide a first aqueous cadaverine composition (9.8% cadaverine and 6.03% $SO_4^{2-}$ in the solution). The same process was carried out on the second cadaverine sulfate composition, and the obtained a second aqueous cadaverine composition (14.90% cadaverine, 5.17% $SO_4^{2-}$ in the solution). Thus, this example showed that according to the methods disclosed herein, salt reduction in a more concentrated cadaverine salt composition was more efficient, and the obtained aqueous cadaverine composition had a lower salt concentration and a higher cadaverine concentration.

Example 8

Solubilities of NaCl and Sodium Sulfate in Aqueous Cadaverine Solutions

At a specific temperature (e.g. 5° C., 18° C., 24° C. or 65° C.), sodium sulfate was added into an aqueous cadaverine solution with a specific cadaverine concentration until a small amount of sodium sulfate was not dissolved. The mixture was stirred for half an hour and allowed to sit for half an hour. The supernatant was removed to detect cadaverine concentration and sulfate concentration. The protocol was repeated for different cadaverine concentrations and/or at different temperatures (Table 2, and FIG. 2).

At a specific temperature (e.g. 5° C., 18° C., 24° C. or 65° C.), NaCl was added into an air-tight system consisting of 50% aqueous cadaverine solution with stirring until a small amount of NaCl was not dissolved. The amount of NaCl added was recorded. Small amounts of water were added just until the insoluble NaCl dissolved completely. The amount of the water added was also recorded. Repeating the addition of salt and water steps described above to obtain the solubilities of NaCl at different cadaverine concentrations (Table 3, and FIG. 3).

TABLE 2

Sodium Sulfate Solubilities in Cadaverine Composition (aq.) at 5° C., 18° C., and 65° C.

| T (° C.) | Cadaverine Concentration (%) | Sodium Sulfate Concentration (%) |
|---|---|---|
| 5 | 5.48 | 5.09 |
|  | 9.71 | 3.33 |
|  | 13.46 | 3.31 |
|  | 17.47 | 1.51 |
|  | 24.14 | 0.97 |
| 18 | 5.61 | 10.46 |
|  | 11.48 | 6.41 |
|  | 17.63 | 4.07 |
|  | 24.62 | 2.57 |
|  | 36.32 | 0.93 |
| 65 | 29.90 | 3.56 |
|  | 31.41 | 3.24 |
|  | 38.82 | 0.77 |
|  | 41.06 | 1.05 |
|  | 51.23 | 0.13 |

TABLE 3

Sodium Chloride Solubilities in Cadaverine Composition (aq.) at 24° C.

| T (° C.) | Cadaverine Concentration (%) | Sodium Sulfate Concentration (%) |
|---|---|---|
| 24 | 41.0053 | 9.4428 |
|  | 39.9805 | 10.0113 |
|  | 38.5559 | 11.1982 |
|  | 36.7162 | 12.1321 |
|  | 33.6967 | 13.1604 |

Example 9

Cadaverine Purification of Cadaverine Sulfate Compositions (I): With Different Solvent Addition Manners ($C_{14}$ Alkane (n-Tetradecane))

A cadaverine sulfate enzymatic conversion solution was concentrated on a rotavap at 50 to 80° C. under −0.09 MPa to a cadaverine sulfate composition (30% cadaverine). Sodium hydroxide was added to the cadaverine sulfate composition at 60° C. and stirred at the same temperature to provide an aqueous cadaverine composition, pH 14.00. The obtained mixture was filtered at 60° C. to provide a filtrate, which was further concentrated on a rotavap at 50 to 90° C. under −0.09 MPa to an aqueous cadaverine composition (47% cadaverine). The amount of cadaverine was the starting amount used to calculate the recovery yield.

100 mL n-tetradecane was used in the cadaverine distillation of the aqueous cadaverine composition (150.00 g, 47% cadaverine) in different manners respectively as described below.

In a first experiment, 10 mL $C_{14}$ alkane was added to the aqueous cadaverine composition (150.00 g, 47% cadaverine) before the cadaverine distillation started. After 30 mL distillate was collected with a heating temperature at 85° C. (oil bath) and a distillation pressure of −0.095 MPa, 20 mL $C_{14}$ alkane mixture was added to the distillation system and the distillation continued with a heating temperature at 85° C. (oil bath) and a distillation pressure of −0.095 MPa for half an hour. Then 70 mL $C_{14}$ alkane mixture was added to the distillation system for further distillation with a final heating temperature at 135° C. (oil bath) and a distillation pressure of −0.095 MPa, until no more distillation was observed. The cadaverine recovery yield was 85.81%.

In a second experiment, 100 mL $C_{14}$ alkane mixture was added to the aqueous cadaverine composition (150.00 g, 47% cadaverine) during the cadaverine distillation via controlled vacuum suction. The $C_{14}$ alkane addition was complete after about 40 mL distillate was collected with a heating temperature at 75° C. (oil bath) and a distillation pressure of −0.095 MPa. The distillation continued with a final heating temperature at 135° C. (oil bath) and a distillation pressure of −0.093 MPa, until no more distillation was observed. The cadaverine recovery yield was 73.27%.

In a third experiment, 100 mL $C_{14}$ alkane mixture was added to the aqueous cadaverine composition (150.00 g, 47% cadaverine) before the cadaverine distillation started. Then the distillation was performed with a heating temperature of 65° C.~135° C. (oil bath) and a distillation pressure of −0.094 MPa, until no more distillation was observed. The cadaverine recovery yield was 86.60%.

In a fourth experiment, 100 mL $C_{14}$ alkane mixture was added to the aqueous cadaverine composition (150.00 g, 47% cadaverine) before the cadaverine distillation started. Then the distillation was performed with a heating temperature of 80° C.~120° C. (oil bath) and a distillation pressure of −0.03 MPa, until about 40 mL distillate was collected. Then the distillation was continued with a final heating temperature of 135° C. (oil bath) and a distillation pressure of −0.096 MPa, until no more distillation was observed. The cadaverine recovery yield was 89.85%.

Example 10

Cadaverine Purification of Cadaverine Sulfate Compositions (II): With Diphenyl Ether A cadaverine sulfate enzymatic conversion solution was concentrated on a rotavap at 50 to 80° C. under −0.09 MPa to a cadaverine sulfate composition (30% cadaverine). Sodium hydroxide was added to the cadaverine sulfate composition at 60° C. and stirred at the same temperature to provide an aqueous cadaverine composition, pH 14.00. The obtained mixture was filtered at 60° C. to provide a filtrate, which was further concentrated on a rotavap at 50 to 90° C. under −0.09 MPa to an aqueous cadaverine composition (47% cadaverine). The amount of cadaverine was the starting amount used to calculate the recovery yield.

The aqueous cadaverine composition (154.4 g, 48% cadaverine) was concentrated on a rotavap at 100° C. at −0.095 MPa until no more distillation was observed. The distillate collected was named distillate A (52.46 g, 25.3% cadaverine). Then 100 mL diphenyl ether was added in the cadaverine distillation system, and the distillation continued with the heating temperature slowly raised to 160° C. (oil bath) and at a distillation pressure of −0.095 MPa, until no more distillation was observed. The distillate collected was named distillate B (72.1 g, 71% cadaverine). The total cadaverine recovery yield was 86.71%.

Example 11

Cadaverine Purification of Cadaverine Chloride Compositions (III): With Dodecanol A cadaverine chloride enzymatic conversion solution (939.82 g, 5.28% cadaverine) was concentrated on a rotavap at 50 to 70° C. under −0.09 MPa to a cadaverine chloride composition (153.01 g, 31.92% cadaverine). Sodium hydroxide (70.00 g, 60% aq.) was added to the cadaverine chloride composition at 60° C. and stirred at the same temperature to provide an aqueous cadaverine composition, pH>14.00. Dodecanol (103.81 g) was added to the obtained mixture before distillation. Then, the distillation was carried out with a heating temperature raised from 80° C. to 150° C. (oil bath) at −0.095 MPa to provide a cadaverine distillate (95.84 g, 38.28% cadaverine). The total cadaverine recovery yield was 73.98%.

Example 12

Cadaverine Purification of Cadaverine Sulfate Compositions (IV): With $C_{14}$-$C_{11}$ alkane mixture (1:1)

Potassium hydroxide (57.31 g) was added to a cadaverine sulfate composition (252.07 g, 21.36% cadaverine) at 80° C. and stirred at the same temperature. Then the mixture obtained was cooled to 30° C. to provide an aqueous cadaverine composition, pH>14.00. $C_{14}$-$C_{11}$ alkane mixture (1:1, about 250 g) was added to the aqueous cadaverine composition before distillation. The distillation was carried out at −0.03 MPa with a slowly raised heating temperature until distillation started. Distillation slowed down when the heating temperature was about 120° C. (oil bath). The distillation was continued at a further reduced pressure slowly adjusted to −0.096 MPa. Then the heating temperature continued raising slowly to 130° C. (oil bath) to continue the distillation until no more distillation was observed. The distillate was collected (210.52 g, 22.17% cadaverine) and the cadaverine recovery yield was 86.68%.

Example 13

Cadaverine Purification of Cadaverine Sulfate Compositions Obtained from 95% Cadaverine: With Glycerol Cadaverine (95%) was mixed with water to provide an aqueous cadaverine composition (250.94 g, 19.99% cadaverine, pH 12.62). The aqueous cadaverine composition was mixed with sulfuric acid (30%, 168.76 g) to provide a cadaverine sulfate composition (pH 7.00). Then NaCl (2.51 g), sodium phosphate (1 g), and glycerol (100.07 g) were added to the cadaverine sulfate composition to provide a cadaverine salt composition (pH 7.85). NaOH (232.61 g, 30.0%) was added to the cadaverine salt composition to provide a composition having a pH of 13.90. The obtained composition was distilled with a slowly raised heating temperature in an oil bath (80~135° C.) at −0.095 MPa. The distillate was collected and the cadaverine recovery yield was 66.46%.

Example 14

Cadaverine Purification of Cadaverine Sulfate Compositions without Solvent Addition and with/without Salt Reduction Step a1-1)

A cadaverine sulfate enzymatic conversion solution was concentrated on a rotavap at 50 to 70° C. under −0.09 MPa to a cadaverine sulfate composition (28.52% cadaverine).

Potassium hydroxide (aq., 47.46 g, 60%) was added to a first cadaverine sulfate composition (150 g, 28.52% cadaverine) at 60° C. and stirred at the same temperature to provide a first aqueous cadaverine composition, pH 13.99.

The first aqueous cadaverine composition was evaporated under −0.095 MPa in an oil bath until no more evaporation was observed. The temperature of the oil bath increased from 80° C. to 180° C. in 130 min. The distillate collected was 143.48 g (aq., 23.12% cadaverine). The recovery yield of cadaverine was 77.52%.

Potassium hydroxide (aq., 47.46 g, 60%) was added to a second cadaverine sulfate composition (150 g, 28.52% cadaverine) at 60° C. and stirred at the same temperature to provide a second aqueous cadaverine composition, pH 13.98. The second aqueous cadaverine composition was filtered at 60° C. to provide a filtrate of 143.36 g (28.14% cadaverine). The solid obtained from the filtration was weighed while it was wet (51.66 g), washed with saturated sodium sulfate (aq., 26.00 g) and filtered to provide another filtrate of 26.55 g (18.65% cadaverine). The filtrates obtained from both filtrations were combined (169.91 g, containing 45.29 g cadaverine) and evaporated under −0.095 MPa in an oil bath until no more evaporation was observed. The temperature of the oil bath increased from 80° C. to 180° C. in 130 min. The distillate collected was 197.38 g (aq., 20.22% cadaverine). The recovery yield of cadaverine was 93.26%.

Example 15

Larger Scale of Cadaverine Purification of Cadaverine Sulfate Compositions without Solvent Addition and with/without Salt Reduction Step a1-1)

A cadaverine sulfate enzymatic conversion solution was concentrated on a rotavap at 50 to 70° C. under −0.09 MPa to a cadaverine sulfate composition (28.52% cadaverine).

Sodium hydroxide (solid) was added to a first cadaverine sulfate composition (100 kg, 28.52% cadaverine) at 60° C. and stirred at the same temperature to provide a first aqueous cadaverine composition, pH 13.99. The first aqueous cadaverine composition was evaporated in a 150 L distillator under −0.095 MPa in an oil bath of 200° C. for 10 hours. The evaporation/distillation system was substantially solid, and could not be stirred. The evaporation/distillation residue after the evaporation/distillation substantially stopped could not be discharged from the distillator because it was substantially solid without fluidity. The recovery yield of cadaverine was 20%.

Sodium hydroxide (solid) was added to a second cadaverine sulfate composition (200 kg, 28.52% cadaverine) at 60° C. and stirred at the same temperature to provide a second aqueous cadaverine composition, pH 14.00. The second aqueous cadaverine composition was centrifuged to remove solid therein and provide a supernatant of cadaverine. The obtained solid was washed with saturated sodium sulfate and filtered to provide a filtrate of cadaverine. The filtrate and the supernatant of cadaverine were combined and concentrated to provide an aqueous cadaverine composition (50 kg, 62% cadaverine), which was distilled under −0.095 MPa in a distillatory (100 L) in an oil bath (200° C.) until no more evaporation was observed (at least 12 hours). The distillate collected was 21 kg (aq., 50% cadaverine). The recovery yield of cadaverine was 33.87%.

Example 16

Larger Scale of Cadaverine Purification of Cadaverine Sulfate Compositions with Salt Reduction Step a1-1): With $C_{14}$ Alkane (n-Tetradecane)

A cadaverine sulfate enzymatic conversion solution was concentrated on a rotavap at 50 to 70° C. under −0.09 MPa to a cadaverine sulfate composition (28.52% cadaverine).

Sodium hydroxide (solid) was added to a cadaverine sulfate composition at 60° C. and stirred at the same temperature to provide a first aqueous cadaverine composition, pH 14.00. The first aqueous cadaverine composition was centrifuged to remove solid therein and provide a supernatant of cadaverine. The supernatant of cadaverine was concentrated to provide a second aqueous cadaverine composition (516.8 kg, 22.90% cadaverine). The second aqueous cadaverine composition was distilled at a reduced pressure (−0.092 MPa) in an oil bath with addition of n-tetradecane (160.00 kg) in one or more portions during the distillation. The temperature of the oil bath increased from 80° C. to 130° C. in 130 min. The distillate was collected, and the recovery yield of cadaverine was about 100%.

Example 17

Cadaverine Purification of Cadaverine Sulfate Compositions Obtained from 95% Cadaverine: With $C_{14}$-$C_{11}$ Alkane Mixture (1:1)

Cadaverine (95%) is mixed with water to provide an aqueous cadaverine composition (250.94 g, 19.99% cadaverine, pH 12.62). The aqueous cadaverine composition is mixed with sulfuric acid (30%, 168.76 g) to provide a cadaverine sulfate composition (pH 7.00). NaOH (232.61 g, 30.0%) is added to the cadaverine salt composition to provide a composition having a pH of 13.90. The obtained composition is distilled with a slowly raised heating temperature in an oil bath (80~135° C.) at −0.095 MPa until the distillation substantially stops. $C_{14}$-$C_{11}$ alkane mixture (1:1, 250 g) is added into the distillation system, and then distillation is continued by fractional distillation.

Example 18

Cadaverine Decomposition after Heated at 160° C.

A purified cadaverine was placed in a 20 mL test tube and heated in a 160° C. oil bath in contact with open air. Samples were removed from the test tube at 0, 2, and 8 hours after the heating started and tested for purity (Table 4).

TABLE 4

| Purity of cadaverine samples after heated at 160° C. | |
|---|---|
| Heating time (hour) | Purity (%) |
| 0 | 98.64 |
| 2 | 98.53 |
| 8 | 97.74 |

The invention claimed is:
1. A method for the purification of cadaverine from an aqueous cadaverine composition comprising one or more involatile impurities, the method comprising:

a) distilling or evaporating the aqueous cadaverine composition wherein one or more solvents are added to the evaporation/distillation system before the evaporation/distillation starts, during the evaporation/distillation and/or after the evaporation/distillation substantially stops when no more evaporation/distillation is observed to produce purified cadaverine; wherein the evaporation or distillation is done at a heating temperature of about 80° C. to about 180° C., and the evaporation or distillation is subjected to a pressure of 1 atm or lower; and the one or more solvents comprise at least one or more high boiling point (HBP) solvents having a boiling point of at least about 185° C. (1 atm).

2. The method of claim 1, wherein the aqueous cadaverine composition is obtained from the following steps:
- a0-1) providing an aqueous cadaverine salt composition;
- a0-0) optionally adding one or more high boiling point solvents; and
- a1) adjusting the pH of the aqueous cadaverine salt composition to provide an aqueous cadaverine composition having a pH of at least about 12.

3. The method of claim 1, wherein the aqueous cadaverine composition is obtained from the following steps:
- a0-2) providing an aqueous cadaverine salt composition comprising a cadaverine production composition, wherein the cadaverine production composition is obtained from a bio-based cadaverine production process;
- a0-0) optionally adding one or more high boiling point solvents; and
- a1) adjusting the pH of the aqueous cadaverine salt composition to provide an aqueous cadaverine composition having a pH of at least about 12.

4. The method of claim 2, wherein Step a1) further comprises:
- a1-1) Removing a solid composition from the aqueous cadaverine composition of step a1).

5. The method of claim 4, wherein step a1-1) further comprises the following steps before step a1-1) is performed:
- a1-11) concentrating the aqueous cadaverine salt composition before the addition of the one or more bases; and/or optionally
- a1-12) concentrating the aqueous cadaverine salt composition/base reaction after the addition of the one or more bases; and/or optionally
- a1-13) concentrating the aqueous cadaverine salt composition/base reaction during the addition of the one or more bases.

6. The method of claim 1, wherein the cadaverine concentration of the aqueous cadaverine composition of step a) is about 5% or higher.

7. The method of claim 1, wherein the cadaverine concentration of the aqueous cadaverine composition of step a) is about 20% or higher.

8. The method of claim 4, wherein step a1-1) disclosed herein comprises:
- a1-31) filtering/centrifuging the first composition to provide a solid and a filtrate/supernatant;
- a1-32) rinsing the solid with an aqueous salt solution and filtering/centrifuging the obtained mixture to provide another solid and another filtrate/supernatant;
- a1-33) optionally repeating step a1-32) until the solid obtained is substantially free of cadaverine; and
- a1-34) combining the filtrates/supernatants obtained from steps a1-31), a1-32) and a1-33) to provide the aqueous cadaverine composition to be further processed in step a).

9. The method of claim 2, wherein the acid anion content of the aqueous cadaverine composition is no more than about 50% of that of the aqueous cadaverine salt composition.

10. The method of claim 2, wherein the acid anion content of the aqueous cadaverine composition is no more than about 70% of that of the aqueous cadaverine salt composition.

11. The method of claim 2, wherein the aqueous cadaverine salt composition comprises one or more cadaverine salts selected from the group consisting of cadaverine sulfate, cadaverine chloride, cadaverine carbonate, cadaverine phosphate and any combinations thereof.

12. The method of claim 2, wherein the aqueous cadaverine salt composition has a pH of about 11 or lower.

13. The method of claim 2, wherein the pH of the first composition of step a1) is about 13.5 or higher.

14. The method of claim 2, wherein step a1) comprises adding an inorganic base composition into the aqueous cadaverine salt composition, wherein the inorganic base composition comprises one or more inorganic bases selected from the group consisting of alkaline metal hydroxides, alkaline earth metal hydroxides, and basic salts thereof.

15. The method of claim 14, wherein the one or more inorganic bases are selected from the group consisting of NaOH, KOH, $Na_3PO_4$, $Na_2CO_3$, and any combinations thereof.

16. The method of claim 1, wherein the aqueous cadaverine composition is distilled at a reduced pressure or ambient pressure in step a).

17. The method of claim 1, wherein the one or more HBP solvents have one or more boiling points of at least about 190° C. (1 atm).

18. The method of claim 1, wherein the one or more HBP solvents are selected from the group consisting of alkanes, chloroalkanes, benzene derivatives, alcohols, ethers, amines, esters, nitriles, and any combinations thereof.

19. The method of claim 18, wherein the one or more HBP solvents are selected from the group consisting of $C_{14}$ alkanes, $C_{11}/C_{14}$ alkane mixture, biphenyl ether, and dodecanol.

20. The method of claim 18, wherein the one or more HBP solvents are alkanes.

21. The method of claim 18, wherein the one or more HBP solvents do not comprise alcohol.

22. The method of claim 1, wherein the purified cadaverine is produced with a recovery yield of at least 66.5%.

* * * * *